United States Patent [19]

McCormack et al.

[11] 4,083,691
[45] Apr. 11, 1978

[54] METHOD FOR DETECTING CONTAMINANTS IN WATER

[75] Inventors: Lawrence M. McCormack; Achille Silvestri, both of Harford; Arthur R. Jones, Jr., Cecil, all of Md.

[73] Assignee: The United States of America as represented by the Secretary of the Army, Washington, D.C.

[21] Appl. No.: 789,769

[22] Filed: Apr. 22, 1977

[51] Int. Cl.² .................. G01N 21/20; G01N 33/18
[52] U.S. Cl. ............................ 23/230 R; 23/230 M; 23/253 R; 23/232 R; 23/254 R
[58] Field of Search ............ 23/230 M, 230 R, 254 R, 23/232 R, 253 R, 253 TP

[56] References Cited
U.S. PATENT DOCUMENTS

| 3,033,655 | 5/1962 | Grosskopf | 23/254 R |
| 3,697,227 | 10/1972 | Goldstein et al. | 23/253 TP |
| 3,811,840 | 5/1974 | Bauer et al. | 23/230 X |

Primary Examiner—R.E. Serwin
Attorney, Agent, or Firm—Nathan Edelberg; Kenneth P. Van Wyck

[57] ABSTRACT

A method for rapidly detecting organic pollutants in water utilizing chemical effervescence to accelerate release of contaminants into the atmosphere above the water sample where they can be detected by conventional air pollution detector tubes. An apparatus for detecting contaminants in the atmosphere above the water solution by detector tube is also disclosed.

12 Claims, 1 Drawing Figure

U.S. Patent  April 11, 1978  4,083,691
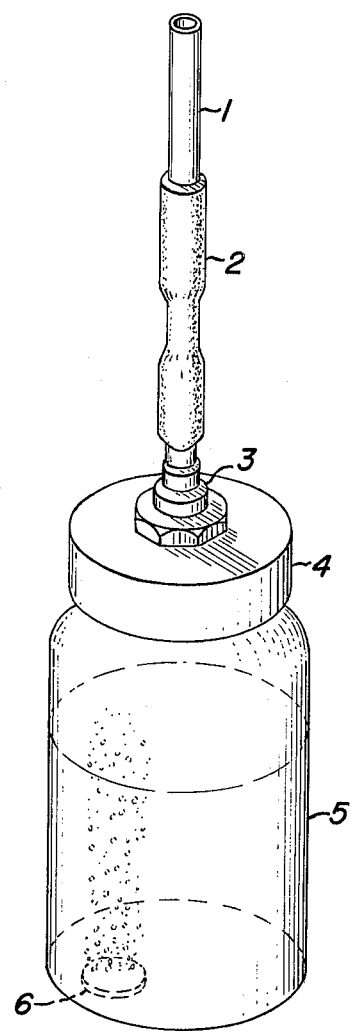

METHOD FOR DETECTING CONTAMINANTS IN WATER

DEDICATORY CLAUSE

The invention described herein may be manufactured, used or licensed by or for the Government for governmental purposes without the payment to us of any royalty thereon.

DESCRIPTION OF THE INVENTION

The invention relates to a method for rapidly detecting organic pollutants in water through use of chemical effervescent materials to accelerate release of contaminants into the surrounding atmosphere where they can be detected by commercially available air contamination detector tubes.

The invention further relates to simplified test apparatus for rapidly detecting organic pollutants in water which can be used in the field to yield sensitive, accurate results.

The present methods for detecting organic pollutants in water rely upon wet chemical analytical techniques requiring trained personnel to perform even the most routine analysis. These existing wet chemical techniques lack sensitivity in detection and are not well-suited for on-site use in the field. Typically, analysis by present procedures is time consuming and requires a number of steps including such preliminary steps as concentration of the test sample, filtering, adjusting the pH and adding additional reagents. The present methods thus require strict control of laboratory techniques unsuited to on-site testing.

The process and test apparatus of this invention has overcome the limitations of the prior methods by simple, self-contained apparatus, utilizing proven air contamination detector tubes, which yield rapid, sensitive and specific identification of organic pollutants by easily determinable colorimetric reactions. The process of this invention provides reproducible accurate differentiation between known pollutants in water when used by non-technical personnel.

The detector tubes used in the process of this invention have been proven to be one of the most effective types of air pollutant detectors in use today, being both widely used in industry as well as in the Army where it is relied upon for detection of chemical warfare agents. The principle and procedures involved in the use of detector tubes for air pollution monitoring is shown in the article of Dr. Karl Grosskopf in CHEMIKER ZIETUNG/CHEM. APPARATUR 87, NO. 8, pages 270–275 (1963) and his U.S. Pat. No. 3,033,655 issued May 8, 1962. Basically, the detector tubes consist of glass tubes containing silica gel held in place by porous retainers. When air is drawn through the tube, the contaminants are visualized by colored reaction with reagents impregnated on the silica gel or by reagents added afterwards from a dropping bottle. Commercially available detector tubes, manufactured by such companies as Bendix/Gastec, Kitagawa and Drager for detecting benzene, cyclohexane, acetone and ethyl acetate, for example, have been found to be useful in this invention.

The principal object of this invention is to provide a sensitive and relatively simple process for rapidly detecting the presence of organic pollutants in water.

A further object of this invention is to provide a simple process of detecting organic pollutants in water through use of a novel method of expanding the proven capability of commercially available air contamination detector tubes to detect contaminants in the air above suspected pollutant containing water.

A still further object of this invention is to provide a method wherein an effervescent material is added to organic pollutant containing water to accelerate the release of said pollutants to the atmosphere where they can be detected by conventional air pollution monitoring techniques.

Another object of this invention is to provide a simple, readily transportable test apparatus for on-site determination of specific pollutants in waterways.

The FIGURE in the drawing shows the test apparatus assembly of this invention.

In particular, the test apparatus assembly of this invention, as shown in the FIGURE, consists of a commercially available detector tube 1, connected by means of a rubber connector tube 2, typically 5 cm in length, to a widemouth, 4 ounce glass jar 5 (approximately 11.5 cm tall) having a rubber lined Bakelite cap 4, threaded to receive a one-quarter inch polypropylene nipple 3. The rubber connector tube 2 is attached to the nipple 3 to hold the detector tube 1 in place. Contained within the jar 5 is a sample of the water to be tested and an effervescent material tablet 6, which is added to the water in the jar to initiate the test for contaminants.

In operation, a detector tube 1 is prepared by breaking the ends of the tube and inserting it into the rubber tubing connector 2 affixed to the cap 4 by nozzle 3. A test is conducted by adding one effervescent material tablet 6, the preferred material being a tablet of citric acid and sodium bicarbonate known commercially by the registered trademark Alka Seltzer, to about 80 ml of water to be tested, which had previously been placed in the jar, and then quickly screwing on the cap 4 with the already connected detector tube 4. The test is allowed to proceed until the effervescence has ceased. A positive test is determined by the normal colorimetric response expected for the particular detector tube being utilized. For example, the silica gel in the benzene detector tube turns brown to indicate a positive test. A standard Army DB-3 detector tube for mustard (dichlorodiethyl sulfide) on the other hand, requires the addition of a base to the detector tube to complete the reaction.

The process of this invention basically depends upon the use of chemical effervescence to accelerate the release of contaminants contained in aqueous solution into the atmosphere above the solution where it can be detected by conventional air pollutant detector tubes. The instant process thus requires the addition of an effervescent material to the water sample to be tested to increase the normally low rate of release of contaminants to the surrounding atmosphere to a level which can be detected, with sensitivity, by available air pollution monitoring procedures. When used with commercially available detector tubes, the process of this invention has shown an increase in detector sensitivity of a factor of 10 over mere sampling of the air over water samples containing industrial pollutants.

The commercial detector tubes which have been found to have utility for this process include commercial detectors for benzene, cyclohexane, acetone and ethyl acetate. Using these aforementioned commercial detectors in this process, it was possible to detect methyl alcohol, acrylonitrile, benzene, phosphorous pentasulfide ($H_2S$ being detected by the detector tube), xylenes and malathion by sampling the air over the mouth of flasks in which these materials were present in a concentration of 1000 mg/ml of distilled water.

The process of this invention can be best shown by reference to the following example test studies which are meant to be illustrative and not in anyway limiting on this invention.

Tests Conducted using Water Containing Industrial Contaminants

Generally, chemical effervescence produced by a citric acid sodium bicarbonate (Alka Seltzer) tablet effected an increase in the sensitivity of a benzene detector tube in six of nine pollutants tested, with a tenfold enhancement over mere sampling of air above the test solution.

Detector tubes for benzene, ethyl acetate, cyclohexane and acetone were effective in detecting organic contaminants in water by this invention. The ethyl acetate, acetone and cyclohexane tubes exhibited some interference from the water vapor inherent in the process, but the use of a drying tube packed with calcium sulfate to remove water vapor, sharpened the detection bands and increased sensitivity.

The table below summarizes the results obtained by this process using a cyclohexane detector tube with a drying tube to detect selected organic pollutants.

| Response of Cyclohexane Detector Tube and Drying Tube to Pollutants | |
|---|---|
| Compound Detected | Concentration Detected (mg/liter) |
| Methanol | 1000 |
| Acrylonitrile | 10 |
| Benzene | 10 |
| Styrene | 6.6 |
| Isoprene | 10 |
| Xylene | 13 |
| Fermate | 120 |
| 2-4-D | 900 |
| 2-4-5T | 280 |

The process of this invention has also been extended to detection of chemical agents in water. Utilizing the effervescence generation process of this invention and a drying tube in conjunction with standard military detectors, it was possible to detect 2 mg/liter mustard solution and cyanide at concentrations of 10 mg/liter of water using the Army AC detector tube.

The process of this invention has potential utility in such areas as detection of trace organic contaminants in fuel, gasoline or other solvents, monitoring chemical reaction side products, monitoring swimming pool chemical assay parameters and determining organic contaminant levels in boiler water.

The particular details of the construction of the test apparatus are not critical in themselves and can be varied within the skill of one in the art. Similarly, the process conditions may be varied to obtain optimum effervescence for detection by the detector tubes or by any other conventional air pollution detector means.

Applicants having disclosed the invention, obvious modifications will become apparent to those skilled in the related chemical art and therefore, applicants desire to be limited only by the scope of the appended claims.

We claim:

1. A method for rapidly detecting the presence of organic pollutants in water comprising the steps of adding an effervescent material to a water sample containing organic pollutants to thereby accelerate the release of pollutants into the atmosphere above the water sample, passing the resulting pollutant containing atmosphere through an air contamination detector tube which has been selected for its colorimetric reactivity with the suspected organic pollutant and then noting any positive colorimetric reaction to indicate the presence of the suspected organic pollutant.

2. The method of claim 1 wherein the effervescent material is a tablet consisting of citric acid and sodium bicarbonate.

3. The method of claim 1 wherein the detector tubes are commercially available detector tubes selected from the group consisting of detectors for benzene, cyclohexane, acetone and ethyl acetate.

4. The method of claim 3 wherein the organic pollutants to be detected in water include methanol, acrylonitrile, benzene, phoshorous pentasulfide, xylenes, styrene, isoprene, fermate and malathion.

5. The method of claim 1 further including the step of using a calcium sulfate drying to remove water vapor for the atmosphere above the water sample to reduce water vapor interference with the detector tube and thereby increase test sensitivity.

6. The process of claim 5 wherein the detector tube used is selected from the group consisting of detectors for ethyl acetate, acetone and cyclohexane.

7. The process of claim 6 wherein the detector tube is a cyclohexane detector tube.

8. In a process for detecting organic pollutants in water through use of air pollution detector tubes for determining the presence of pollutants in the air above the water, the improvement comprising the step of adding an effervescent material to the water being tested to accelerate the release of pollutants into the air where they may be more rapidly detected with increased sensitivity.

9. The process of claim 8 wherein the effervescent material is a tablet consisting of citric acid and sodium bicarbonate.

10. A test apparatus system for detecting organic pollutants in water through use of an air contaminant detector tube for monitoring the atmosphere above the water being tested consisting essentially of a glass jar container means with a rubber lined cap which has been threaded to receive a nipple means, a nipple fitted into said cap for allowing flow of the atmosphere within the jar to a detector tube which is attached to said nipple by means of a rubber connector tube which also serves to hold the detector tube in place above said jar, and an effervescent material tablet which is added to the water being tested contained within said jar container.

11. The test apparatus system of claim 10 further including a calcium sulfate drying tube for removing water vapor from the atmosphere above the water being tested to eliminate water vapor interference with the detector tube.

12. The test apparatus system of claim 10 wherein the effervescent material tablet consists of citric acid and sodium bicarbonate.

* * * * *